(12) United States Patent
Scheuringer

(10) Patent No.: US 7,491,542 B2
(45) Date of Patent: Feb. 17, 2009

(54) TEST DEVICE FOR DETERMINING THE CONCENTRATION OF LDL-CHOLESTEROL IN A SAMPLE

(76) Inventor: Kim Scheuringer, Albrechtsgasse 74, 2500 Baden (AT)

( * ) Notice: Subject to any disclaimer, the term of this patent is extended or adjusted under 35 U.S.C. 154(b) by 517 days.

(21) Appl. No.: 10/889,988

(22) Filed: Jul. 12, 2004

(65) Prior Publication Data

US 2006/0008914 A1    Jan. 12, 2006

(51) Int. Cl.
*G01N 33/92* (2006.01)
*G01N 21/78* (2006.01)

(52) U.S. Cl. .................. 436/71; 436/63; 436/164; 436/165; 436/166; 436/169; 436/174; 436/175; 436/177; 436/178; 422/55; 422/56; 422/58; 422/99; 422/101; 435/11; 435/19; 435/26

(58) Field of Classification Search .............. 436/63, 436/71, 164, 165, 166, 169, 170, 172, 174, 436/175, 177, 178, 57; 422/55, 56, 57, 58, 422/99, 101; 435/11, 19, 26
See application file for complete search history.

(56) References Cited

U.S. PATENT DOCUMENTS

| | | | |
|---|---|---|---|
| 4,544,630 A | 10/1985 | Ziegenhorn et al. | |
| 4,746,605 A | 5/1988 | Kerscher et al. | |
| 5,340,539 A | 8/1994 | Allen et al. | |
| 5,401,466 A * | 3/1995 | Foltz et al. | 422/56 |
| 5,411,870 A * | 5/1995 | Law et al. | 435/11 |
| 5,532,172 A | 7/1996 | Ziegenhorn et al. | |
| 5,597,532 A | 1/1997 | Connolly | |
| 5,795,786 A | 8/1998 | Boos et al. | |
| 5,804,450 A | 9/1998 | Karl | |
| 5,807,696 A | 9/1998 | Miyauchi | |
| 5,814,472 A | 9/1998 | Miki et al. | |
| 5,888,827 A | 3/1999 | Kayahara et al. | |
| 6,057,118 A * | 5/2000 | Nakamura et al. | 435/11 |
| 6,107,045 A * | 8/2000 | Koren et al. | 435/7.1 |
| 6,342,364 B1 * | 1/2002 | Watanabe et al. | 435/11 |
| 6,524,864 B2 | 2/2003 | Decastro | |
| 6,558,897 B2 | 5/2003 | Scheuringer | |
| 6,794,157 B1 * | 9/2004 | Sugiuchi | 435/11 |
| 6,991,913 B1 * | 1/2006 | Wieland et al. | 435/18 |
| 2004/0023400 A1 | 2/2004 | Tamura et al. | |
| 2004/0126830 A1 | 7/2004 | Shull et al. | |
| 2004/0146957 A1 | 7/2004 | Watanabe et al. | |
| 2005/0170447 A1 * | 8/2005 | Lawrence et al. | 435/11 |
| 2005/0221502 A1 * | 10/2005 | Shindelman et al. | 436/514 |

FOREIGN PATENT DOCUMENTS

WO    WO 00/78998    12/2000

OTHER PUBLICATIONS

Sugiuchi et al. Clinical Chemistry, vol. 44:3, 1998, pp. 522-531.*

(Continued)

*Primary Examiner*—Maureen M Wallenhorst
(74) *Attorney, Agent, or Firm*—Ladas & Parry LLP

(57) ABSTRACT

The present invention provides a test device for determining the concentration of LDL-cholesterol in a sample. The test device has a continuous solid surface with at least one reaction area on the continuous solid surface, and the reaction area has, in dry form, a non-LDL inhibitor and a system for determining the concentration of cholesterol.

48 Claims, 8 Drawing Sheets
(5 of 8 Drawing Sheet(s) Filed in Color)

OTHER PUBLICATIONS

Paek Se-Hwan et al; "Immunochromatographic membrane strip assay system for a single-class plasma lipoprotein cholesterol, exemplified by high-density lipoprotein cholesterol measurement;" Biotechnol BioEng: Biotechnology and Bioengineering, Jan. 20, 1999, John Wiley & Sons Inc., New York, NY, USA, vol. 62, No. 2.

* cited by examiner

TEST DEVICE FOR DETERMINING THE CONCENTRATION OF LDL-CHOLESTEROL IN A SAMPLE

FIELD OF THE INVENTION

The present invention relates to a test device for determining the concentration of cholesterol from low density lipoproteins in a sample.

COLOR DRAWINGS

The file of this patent contains at least one drawing executed in color. Copies of this patent with color drawing(s) will be provided by the Office upon request and payment of the necessary fee.

BACKGROUND OF THE INVENTION

Cholesterol, triacylglycerol and other lipids are transported in body fluids by lipoproteins which are classified according to their density: chylomicrons, chylomicron remnants, very low density lipoproteins (VLDL), intermediate density lipoproteins (IDL), low density lipoproteins (LDL) and high density lipoproteins (HDL). A lipoprotein is a particle with a nucleus made of hydrophobic lipids which nucleus is surrounded by a cover of polar lipids and apoproteins. Lipoproteins have two functions: they solubilize highly hydrophobic lipids and they comprise signals which help regulate the transport of specific lipids to specific cells and tissues.

Triacylglycerol, cholesterol and other lipids taken up with food are transported with chylomicrons from the intestine to fatty tissue and to the liver.

Endogenous triacylglycerols are synthesized in the liver and transported by VLDL. Lipase helps release triacylglycerols from the VLDL; the substance remaining after such release is high in cholesterol and called the IDL. The IDL may be taken up and metabolized by the liver or transformed into LDL, which is the main cholesterol carrier of the blood. The function of these LDL particles is to transport cholesterol to peripheral tissues and to help control de novo cholesterol production. It has been shown that high levels of LDL-Cholesterol in the blood correlate with atherosclerosis which is a progressive disease characterized in part by sedimentation of lipids in inner walls of arteries, particularly of coronary arteries. It has also been shown that a high blood level of LDL-Cholesterol correlates with coronary heart disease. Also, a negative correlation exists between blood levels of HDL cholesterol and coronary heart disease.

The level of total cholesterol in blood, which is the sum of HDL-Cholesterol, LDL-Cholesterol, VLDL-Cholesterol and chylomicron-Cholesterol, is not considered an adequate indicator of the risk of coronary heart disease and atherosclerosis. It is important to determine the amount of LDL-Cholesterol in a patient, for instance as an indication of such risk or for other reasons that may be related to health. Various methods of measuring LDL-cholesterol have been described in the state of the art:

1. Electrophoretic separation with following visualization of lipoprotein bands by polyanion precipitation and conversion of turbidity units into cholesterol values.

2. Ultracentrifugation
This method requires special apparatus and is very time consuming.

3. LDL-Cholesterol can be furthermore calculated with the help of the Friedewald formula whereby the total cholesterol, HDL cholesterol and triglycerol values are determined in a sample. LDL-Cholesterol=total cholesterol−HDL cholesterol−⅕ triglyceride. However, this calculation contains an error of about 10%.

4. Precipitation reactions.
Various reactions are described, for example a method where LDL is precipitated with the help of lectin and the amount of cholesterol before and after precipitation is determined and the amount of LDL-Cholesterol is calculated.

*Handbook of Lipoprotein Testing*, 2d ed., Eds. Nader Rifai, G. Russell Warnick, Marek H. Dominiczak: AACC Press (2000), Chapters 9 and 12.

However, these methods are time consuming and not suitable for routine and high throughput testing, or for testing by a subject for instance at home, without a need for professional assistance. Therefore, there is a need for more efficient LDL-Cholesterol tests. Various publications relate to these aspects:

U.S. Pat. Nos. 5,532,172 and 4,746,605 both relate to a method for determining the LDL-Cholesterol concentration in a sample, whereby in a first step HDL is separated with the help of HDL specific antibodies. After separation, the remaining LDL-Cholesterol is determined.

U.S. Pat. No. 6,057,118 discloses a method for measuring the LDL-Cholesterol concentration in a sample whereby a surfactant is added to the sample to block LDL-cholesterol. Other forms of cholesterol such as HDL-Cholesterol and VLDL-Cholesterol are then reacted with a cholesterol-assaying enzyme reagent, and the remaining amount of LDL-cholesterol is determined thereafter. By measuring cholesterol at a certain period of time after addition of the surfactant, only the LDL-Cholesterol is determined.

U.S. Pat. No. 5,807,696 discloses a method wherein LDL is inhibited, HDL-Cholesterol is used by reaction with enzymes, after which the remaining LDL-Cholesterol is determined.

U.S. Pat. No. 5,888,827 discloses a test system in liquid phase where the addition of a sugar compound and a protein solubilizing agent results in different reactivities of the different compounds HDL, LDL, VLDL and chylomicrons. After selecting and adding a combination of two reagents a chromogenic substance is added with which the LDL-Cholesterol is determined.

U.S. Pat. No. 4,544,630 discloses a method in which LDL-Cholesterol is determined at a specific time. By adding a specific surfactant at a pH of 6.5 to 8.0, LDL-Cholesterol reacts before HDL-Cholesterol. Therefore, by measuring the amount of cholesterol at a defined moment, only the amount of LDL-Cholesterol is determined. This method requires a meter and computer for analysis of the amount of LDL-cholesterol in a sample.

U.S. Pat. No. 5,804,450 discloses a liquid method and reagent for determining LDL in serum samples by adding an LDL precipitating agent, an LDL aggregating agent and a zwitterionic detergent to a sample, and then detecting LDL aggregates.

U.S. Pat. No. 5,795,786 discloses a liquid method and reagent for determining LDL in serum samples by adding an LDL aggregating agent and taking turbidimetric measurements of the LDL aggregate.

A similar method is described in U.S. Pat. No. 6,524,864 where a test strip is provided with an LDL precipitating agent, such as dextran, on a first layer after which HDL passes through a second layer and reacts on a reaction pad containing cholesterol esterase, cholesterol oxidase, peroxidase, surfactants and TMB (tetramethylbenzidine chromogen). A difference between total cholesterol and HDL cholesterol values yields LDL-Cholesterol values.

U.S. Pat. No. 5,340,539 discloses a method for using a "thermometer"-shaped device to determine the amount of total cholesterol or total cholesterol ester in a sample.

U.S. 2004/0126830 A1 discloses indirectly measuring LDL-cholesterol by measuring total cholesterol and the sum total of HDL, VLDL and chylomicron cholesterol, and then calculating the amount of LDL-cholesterol by subtracting from the measured amount of total cholesterol the measured amount of the sum total of HDL, VLDL and chylomicron cholesterol. The sum total of cholesterol of HDL, VLDL and chylomicrons is measured by adding a surfactant to inhibit LDL-cholesterol and allow for the detection of HDL, VLDL and chylomicron cholesterol before LDL-cholesterol is detected.

U.S. 2004/0023400 discloses an assay for measuring HDL cholesterol by using a surfactant to increase the solubility of HDL and another surfactant to inhibit lipoprotein other than HDL from dissolving.

SUMMARY OF THE INVENTION

No method for measuring LDL-cholesterol has yet been provided which can be carried out by the patient himself, at home without further laboratory apparatus or medical aid. Therefore, it is desirable to provide a test device which a patient can carry out by himself without further technical or medical help which test device is simple, inexpensive and provides results within minutes and in a way that no further calculation or additional analytical steps are necessary. It is also an object of the present invention to overcome the aforementioned deficiencies in the prior art and to provide a test device which does not require liquid phase detection of LDL-cholesterol.

The present invention is directed to a test device comprising a solid surface with at least one reaction area, said at least one reaction area being provided with
   an Non-LDL inhibitor and
   a system for determining the concentration of cholesterol.

The present invention further relates to a method for determining a concentration of LDL-Cholesterol in a sample comprising the steps of
   providing a test device comprising a solid surface with at least one reaction area, said at least one reaction area being provided with
   a) an Non-LDL inhibitor and
   b) a system for determining the concentration of cholesterol;
   applying to said at least one reaction area said sample;
   letting said sample react with said system in order to obtain a reaction result; and
   determining the concentration of cholesterol with said reaction result.

According to a preferred embodiment, said Non-LDL inhibitor is a polymer, preferably a nonionic polymer, still preferably at least one polymer selected from the group consisting of polyoxymethylene, polyoxyethylene, polyoxypropylene, and polyoxybutylene. Said polymer may include a copolymer. A preferred copolymer comprises polyoxyethylene and polyoxypropylene and said copolymer has preferably an average molecular mass of 500 to 10000 Da, preferably 1000 to 6500 Da.

Also preferred is the use of other substances than polymers as an Non-LDL inhibitor, including but not limited to dodecylbenzene, higher alcohol and fatty acid.

The present invention further relates to a test device whereby the Non-LDL inhibitor is provided on the reaction area in a concentration of about 1 mg/m$^2$ to about 500 g/m$^2$.

Preferably, the Non-LDL inhibitor is present in an amount of about 1 mg/m$^2$ to about 200 g/m$^2$, even more preferably about 1 g/m$^2$ to about 100 g/m$^2$, even more preferably present in an amount of about 3 to 30 g/m$^2$, and most preferably present in an amount of about 10 to about 20 g/m$^2$.

According to a further embodiment, the present invention relates to a test device wherein the Non-LDL inhibitor is a non-LDL antibody, preferably an anti-HDL antibody.

According to a preferred embodiment of the present invention, said system for determining the concentration of cholesterol comprises an enzyme system comprising cholesterol esterase and cholesterol oxidase, or comprising cholesterol esterase and cholesterol dehydrogenase.

The present invention further relates to a test device wherein the system for determining the concentration of cholesterol comprises a chromogen. Preferably the system further comprises at least one reference area comprising a colored surface as reference to a given concentration of cholesterol. More preferably, it comprises at least two reference areas each comprising a colored surface as references to given concentrations of cholesterol. More preferably, said at least one reaction area is at least partly movably attached to said at least two reference areas in order to compare colors developed by said chromogen on said at least one reaction area with said colored surfaces of said at least two reference areas.

The present invention further relates to a test device wherein said system for determining the concentration of cholesterol comprises a fluorescent substance or a radioactive isotope.

According to a further embodiment of the present invention, said Non-LDL inhibitor includes a substance for inhibiting chylomicron and VLDL. Preferably, said substance is a-cyclodextrin sulfate.

A further preferred test device according to the present invention comprises at least one membrane covering at least part of said reaction area, said membrane being selective for interfering substances, preferably for erythrocytes.

According to a further embodiment, said sample is selected from the group consisting of whole blood and serum.

DETAILED DESCRIPTION OF THE INVENTION

Figure 1A:
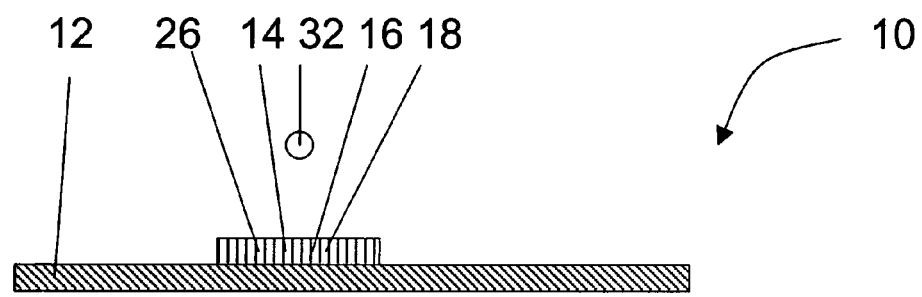
FIG. 1a is a diagram illustrating a side view of a test device of the invention.

The embodiments of the present invention described in the application are not intended to be exhaustive or to limit the invention to the precise forms disclosed in the application. Rather the embodiments are chosen and described so that others skilled in the art may appreciate and understand the principles and practices of the present invention, and in particular the preferred embodiment of this application.

Definitions

"VLDL" refers to very low density lipoprotein.

"LDL" refers to low density lipoprotein. LDL may include cholesterol.

"LDL-Cholesterol" refers to Cholesterol within low density lipoprotein.

"Non-LDL" refers to cholesterol-carrying lipoprotein(s) that are not LDL.

"HDL" refers to high density lipoprotein.

"Polymer" refers to a large molecule having repeated chemical units.

The term "membrane being selective for interfering substances", or generally "membrane" in the context of this invention, relates to any kind of membrane able to retain molecules that may interfere either with the reaction on the reaction area between the sample and the system for determining the concentration of cholesterol or with the interpretation of the reaction result, for example molecules which have their own color and which color would change the resulting color developed on the reaction area by for example a chromogen. Preferably, such membrane is a blood separation membrane, including but not limited to a membrane that separates erythrocytes from whole blood, keeping the erythrocytes from such interfering as directed above. The blood separation membrane may be for instance a glass fiber membrane or a polycarbonate membrane. An example of a suitable commercial glass fiber membrane is Ahlstrom Grade 144, thickness 0.378 mm, available from Ahlstrom Filtration, Inc., Mt. Holly Springs, Pa. However, the thickness and other qualities of this example are meant to illustrate but not limit the invention, as any membrane selective as discussed above is appropriate in this invention. Depending on the sample and the system for determining the concentration of cholesterol the person skilled in the art will know in advance which molecules may interfere and will be able to select a membrane which will retain these interfering molecules from accessing the reaction area.

"Solid surface" includes any sort of porous substance that has or will have a reaction area, such as paper or a membrane, preferably a substance conventionally used in test strips for testing devices such as the present device. A solid surface of this invention may also comprise a film, made either before substances forming a reaction area, or concurrently with reaction area substances. For instance, a film-forming reagent, such as a monomer that polymerizes under certain conditions, may be mixed with the Non-LDL inhibitor and/or system for determining the concentration of cholesterol and applied (for instance sprayed, soaked, painted) onto a support such as a strip of plastic or paper. In this case, the solid surface develops as the film forms with the reaction area intermixed with the film.

Typically, a solid surface of this invention is continuous and flat; that is, the surface does not have large ridges or bumps or gaps. However, a solid surface of this invention may have different shapes, for instance the solid surface may be a well, coated with for instance a system for detecting cholesterol concentration and dried, and used in conjunction with a liquid Non-LDL inhibitor solution and sample placed in the well. Or alternatively the Non-LDL inhibitor could be coated and dried onto the well, and the system for detecting cholesterol concentration added to the well in liquid form.

Preferably, the test device of this invention is made by soaking a solid surface with a chemical solution having the Non-LDL inhibitor and system for determining the concentration of cholesterol, and then drying it. Such soaking may occur for instance by dipping the surface into one or more such chemical solutions, and/or coating the surface with one or more such chemical solutions, and allowing the solutions to dry on the surface. The solid surface may be a variety of shapes and sizes, most preferably a shape and size suitable for a test device that may be used at home. Preferably, the solid surface is about 3 to 10 cm long, more preferably about 5 cm long. Preferably, the solid surface is about 1 to 10 cm wide, more preferably about 1 cm wide. Preferably, a solid surface made of paper or similar substance is about 0.01 cm to 1 cm deep, more preferably about 0.05 cm deep. Preferably, a solid surface formed as a film is about 0.1 mm thick. A solid surface may be attached to and supported by other structures, for instance such as a thermometer-type apparatus or the apparatus pictured in FIGS. 5-7 of this application.

The test device is intended to absorb sample as needed. In the event that an excess of sample is present, the excess of sample will not be absorbed into the test device. A test device of this invention may further include an overflow pad made of paper or glass fiber that may be applied to soak and/or draw off excess sample.

"Serum" relates to the non-cellular portion of blood from which cellular components such as erythrocytes are excluded and which does or does not include fibrinogen.

The term "Non-LDL inhibitor" relates to any molecule or agent which allows the system for determining the concentration of cholesterol to react preferably or more quickly with LDL-Cholesterol than with non-LDL cholesterol. Preferably, the Non-LDL inhibitor prevents at least 80% of non-LDL-cholesterol from reacting with the system for determining the concentration of cholesterol. More preferably, the Non-LDL inhibitor prevents at least 90% of such reaction, even more preferably prevents at least 92% of such reaction, even more preferably prevents at least 94% of such reaction, even more preferably prevents at least 96% of such reaction, even more preferably prevents 98% of such reaction, even more preferably prevents 99% of such reaction, and most preferably prevents all (100%) of non-LDL-cholesterol from reacting with the system for determining the concentration of cholesterol. Without being bound by theory, it is believed that in the presence of Non-LDL inhibitor either the non-LDL particles aggregate to macroparticles and are resistant to the system for determining the concentration of cholesterol so that the non-LDL-cholesterol does not react in the system, that the Non-LDL inhibitor reduces/inhibits non-LDL reaction with the system for determining cholesterol, and/or that the Non-LDL inhibitor activates LDL cholesterol so that LDL cholesterol reacts with the system and non-LDL cholesterol does not.

Figure 7:
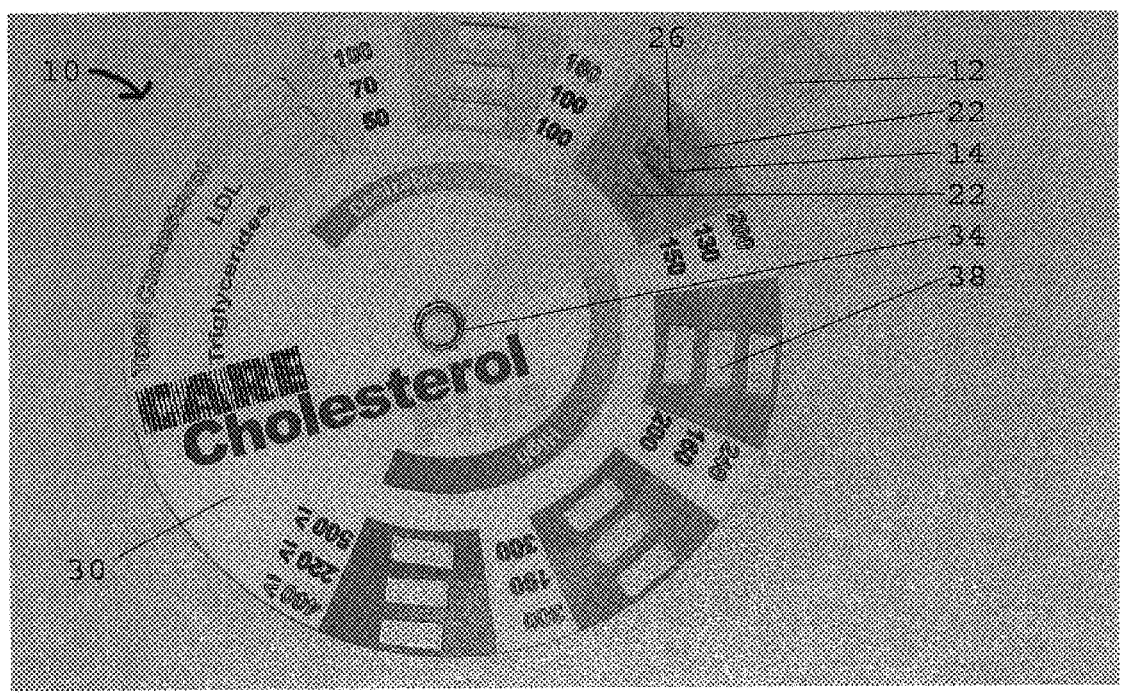
FIG. 7 is a color photograph showing a plan view of a working test device of FIG. 6, three minutes after taking the photograph of FIG. 6.

The term "system for determining the concentration of cholesterol" relates to a combination of substances necessary for measuring the concentration of LDL-cholesterol in the sample applied to the reaction area. The system may be for example a combination of enzymes, chemical agents, buffers, salts, stabilizers, etc. There are many systems including reactions known to the person skilled in the art that are used for determining the concentration of cholesterol; the necessary substances for carrying out these reactions can be easily selected and applied to the reaction area. Preferably the Non-LDL inhibitor is present on the reaction area with said system. However, the Non-LDL inhibitor may also be present in the reaction area but placed at a distance from said system. For example, the sample can be placed on the reaction area where the Non-LDL inhibitor is provided and, after or while the sample and the Non-LDL inhibitor interacts the sample moves for instance by simple diffusion along the reaction area or intervening are of the test device to the system for determining the concentration of cholesterol. The cholesterol in this sample then reacts with this system in order to obtain a result with which the concentration of cholesterol is determined. The concentration of cholesterol may be read for instance by comparing a developed color to reference colors, as shown in FIG. 7, or by measuring the conductivity of a reaction area for instance changed by $H_2O_2$ production in a given system. Such conductivity is measured by a conductivity meter, or other ways to measure conductivity as are or would be known by those skilled in the art. (For instance, by an Accutrend® meter of Roche Diagnostics (F. Hoffmann-La Roche Ltd, Basel, Switzerland).

Several systems for determining the concentration of total cholesterol of a sample are known in the art. For instance, commercially available systems include total cholesterol tests from Chematics, Inc.(Chematics, Inc., North Webster, Ind., USA), Lifestream Inc. (510 Clearwater Loop, Post Falls, Id., USA), PTS Inc. (Polymer Technology Systems, Inc., Indianapolis, Ind., USA), Cholestrak(AccuTech LLC, Vista, Calif., USA), Accu-Trend® (Roche Diagnostics, F. Hoffmann-La Roche Ltd, Basel, Switzerland).

The time needed for a system for determining the concentration of cholesterol according to this invention may take from 0.1 seconds to 1 hour, preferably 1 second to 20 minutes, even more preferably 1 minute to 10 minutes, and more preferably still 3 minutes to 9 minutes.

A test device and method of the present invention comprises for example the movement of a sample (after exposure to the Non-LDL inhibitor of this invention) along a reaction path similar to the shape of a thermometer, similar to the disclosure of U.S. Pat. No. 5,340,539. On this reaction path the system for determining the concentration of cholesterol can be placed, whereby the further the sample moves along the reaction path the higher the concentration of cholesterol is in the sample. The present invention further includes a test device where, for instance, the Non-LDL inhibitor is dried on a reaction area of a solid surface, and the system for determining the concentration of cholesterol is present in liquid form. Similarly, the system for determining the concentration of cholesterol may be dried on the reaction area of the solid surface, and the system for determining the concentration of cholesterol present in liquid form.

The term "reaction area" comprises both the Non-LDL inhibitor and the system for determining the concentration of cholesterol, whether they appear in the same physical space or at some distance from each other. Exposure of the sample to the Non-LDL inhibitor may occur prior to or concurrently with exposure of the sample to the system for determining cholesterol concentration. A reaction area of this invention may have a variety of shapes and sizes, including for instance a square, a rectangle, a circle, an oval, a trapezoid or any given irregular shape. The size of a reaction area of this invention is preferably about the size of a window in a colored reference area, for instance as shown in FIG. 7. A reaction area is preferably located on one continuous area of a solid surface of this invention, but may be located on more than one solid surface. Preferably, a reaction area has a rectangular shape of about 0.1 cm to 2 cm, preferably 0.3 cm on one side, and about 0.1 to 2 cm, preferably 0.8 cm on the other side. The depth of a reaction area may be limited to the depth of the chemical film placed on top of a solid surface, but may also include saturated portions of the solid surface.

The test device according to the present invention comprises a solid surface, which is for example a paper, a membrane, or any other material conventionally used for performing analytical tests. The test device may comprise one reaction area, however, it may also comprise two or more reaction areas depending for instance on the number of samples to be tested or the number of parallel reactions to be carried out. For instance, the present invention further comprises a test device having additional reaction areas for parallel testing of other substances, such as total cholesterol, triglycerols, the presence of specific antibodies or antigens, blood type, etc. However, at least one reaction area on the test device is provided with an Non-LDL inhibitor according to the present inventin. See for instance FIG. 7.

Examples of polymers and other substances useful as Non-LDL inhibitors in the present invention are:
Polyoxyethylene lauryl ether,
Polyoxyethylene cetyl ether,
Polyoxyethylene stearyl ether,
Polyoxyethylene oleyl ether,
Polyoxyethylene behenyl ether,
Polyoxyethylene monolaurate,
Polyoxyethylene monostearate,
Polyoxyethylene monooleate,
Polyoxyethylene laurylamine,
Polyoxyethylene stearylamine,
Sucrose fatty acid ester,
Sodium dodecylbenzenesulfonate,
Sodium n-dodecylbenzenesulfonate,
Sodium lauryl sulfate, and
Higher alcohol sulfuric acid ester sodium salt It has been shown that in particular nonionic polymers or other substances preferably selected from the group consisting of polyoxymethylene, polyoxyethylene, polyoxypropylene, polyoxybutylene, dodecylbenzene, higher alcohol, and fatty acid are suitable. In particular a copolyether comprising polyoxyethylene and polyoxypropylene (POE-POP) has been shown to be an effective Non-LDL inhibitor in the present invention. Preferably, at least one Non-LDL inhibitor of a test device of this invention is POE-POP. It is believed that POE-POP induces bending of HDL to microparticles so that HDL-cholesterol has reduced reactivity with the systems for detecting the concentration of cholesterol. Therefore, when subsequent cholesterol tests are carried out, the cholesterol from the HDL fraction is not taken into account. The Non-LDL inhibitor as well as the system for determining the concentration of cholesterol are for example impregnated on or in the reaction area or are for example covalently bound thereto. They are applied to the reaction area by for example dipping into or otherwise coating the reaction area (for instance with a brush) with a solution comprising the Non-LDL inhibitor and the necessary agents for the system for determining the concentration of cholesterol or by for example laying an amount of such a solution onto said reaction area and letting the reaction area dry.

Polyoxyethylenealkylene phenyl ethers and polyoxyethylenealkylene tribenzylphenyl ethers may also be used as Non-LDL inhibitors of the present invention. Examples of the former ethers include Emulgen A-60 (Kao Corporation, Kayabacho Head Office, 1-14-10 Nihonbashi Kayabacho, Chuo-ku, Tokyo 103-8210, Japan) and examples of the latter ethers include Emulgen B66 (Kao Corporation). The surfactants may be used singly or in combination with one or more other Non-LDL inhibitors.

It has surprisingly been shown that the test device produces good results on a solid support, e.g. without first needing to provide a liquid phase of all sample and reagents and then eventually separating the liquid into different fractions, in particular the LDL-Cholesterol fraction to be detected from Cholesterol of HDL, VLDL and chylomicrons. Furthermore, any buffers, stabilizers and other agents necessary for carrying out for instance non-LDL-Cholesterol inhibition and cholesterol detection reactions related to the system for detecting the concentration of cholesterol are preferably present on the reaction area. The substances and agents may be—as already mentioned—immobilized to the reaction area by for example covalent binding or similar forces, depending on the substances and the chemistry of the reaction area.

In case the Non-LDL inhibitor is an anti-HDL antibody, the antibody is for instance a monoclonal or a polyclonal antibody which is specific for HDL and inhibits reaction of HDL-Cholesterol with the agents comprised in the system for determining the concentration of cholesterol. The production of HDL and other non-LDL antibodies is well known to the person skilled in the art.

The system for determining the concentration of cholesterol preferably comprises a color reaction on the reaction area which color then can be compared to reference areas. Hereby, the reference areas may be separated from the part of the test device comprising the reaction area, for example in form of a strip or which with a number of colors, each color referring to a specific concentration of cholesterol. Furthermore, it is preferred to provide on the reference area the concentration of cholesterol to which the color of reference corresponds to. For example, the concentrations 70, 100, 130, 160, 190 and 220 mg/dl cholesterol can be marked to the respective color. It is furthermore preferable to indicate one or more concentrations of cholesterol considered normal and one or more concentrations of cholesterol considered critical for health. See for example the colored reference areas of the colored surface of the wheel (30) of FIG. 7.

It is furthermore preferable to provide a reaction area which is at least partly movably attached to the reference area, whereby said movable part comprises said system for determining the concentration of cholesterol. See for instance, the embodiment of the test device shown in FIGS. 5-7. Of course, also the complete reaction area—with Non-LDL inhibitor—may be movably attached to the reference area. For example an elongated test strip with a reaction area is provided, said elongated test strip being attached on one end to the center of a surface comprising a number of reference areas. After applying a sample and developing a colored result the reaction area of the test strip may be turned and thereby moved from one or more reference areas to other(s) in order to easily compare the color of the reaction area with the color of the reference area. It is of course possible to provide more than one test strip to the solid surface comprising the reference areas.

A further possibility for the system for determining the concentration of cholesterol is by applying a sample to a reaction area which is provided for example as a well, in which the Non-LDL inhibitor is provided and where HDL inhibition or LDL activation takes place. After this reaction the sample moves up or along said system for determining the cholesterol concentration. This may be provided in a solid surface similar to a thermometer, whereby the higher the sample moves up the greater the concentration of cholesterol is in the sample. An example for a similar test system is CholesTrak by Accutech LLC, whereby the total cholesterol is measured, as also described in U.S. Pat. No. 5,340,539.

The determination of the concentration of cholesterol takes place with the use of methods and systems known for this purpose. The determination can therefore for example be carried out by saponification with alcoholic potassium hydroxide solution and chemical determination according to Liebermann-Burchhard. (Handbook of Lipoprotein Testing, 2d ed., Eds. Nader Rifai, G. Russell Warnick, Marek H. Dominiczak: AACC Press (2000), Chapter 9). Furthermore, it is possible to use enzymatic determination with the use of a cholesterol oxidase and a cholesterol ester splitting enzyme or enzyme system, such as especially cholesterol esterase. In this case, the amount of consumed oxygen, the amount of cholestenon formed or preferably the amount of hydrogen peroxide formed can be determined, using methods known for this purpose. This process is suitable in combination with for instance a colorimetrical cholesterol determination method. For example, an oxidizable color forming agent may be used in the system for determining the concentration of cholesterol which can react with hydrogen peroxide in the presence of a peroxidase to cause color formation. This can be a combination of a coupler, for example thioaminoantipyrine with a developer forming color by oxidative condensation with the coupler including a combination of thioaminoantipyrine with a phenol compound, a naphthol compound or an aniline compound, a combination of a hydrozone with an aniline compound etc. and by a color former which forms a color by itself by oxidation which are well known in the art. Such a chromogen may be tetramethylbenzidine.

In the event that an enzyme system using cholesterol esterase is used, preferably the cholesterol esterase is present in a reagent for coating a solid surface of this invention an amount of from in an amount of 1 nano-kat/l to 100 kat/l. Even more preferably, said enzyme is present in an amount of 0.1 mkat/l to 10 mkat/l. Even more preferably, said enzyme is present in an amount of 1 mkat/l to 6 mkat/l. Preferably, the cholesterol esterase is present on the test device in an amount of about 1 nano-kat/$m^2$ to about 1 kat/$m^2$, more preferably about 1 micro-kat/$m^2$ to about 10 mkat/$m^2$, even more preferably about 0.1 mkat/$m^2$ to about 1 mkat/$m^2$.

In the event that an enzyme system using cholesterol oxidase is used, preferably the cholesterol oxidase is present in an amount of 1 nano-kat/l to 100 kat/l. Even more preferably, said enzyme is present in an amount of 0.1 mkat/l to 10 mkat/l. Even more preferably, said enzyme is present in an amount of 1 mkat/l to 6 mkat/l. Preferably, the cholesterol oxidase is present on the test device in an amount of about 1 nano-kat/$m^2$ to about 1 kat/$m^2$, more preferably about 1 micro-kat/$m^2$ to about 10 mkat/$m^2$, even more preferably about 0.1 mkat/$m^2$ to about 1 mkat/$m^2$.

In the event that an enzyme system using cholesterol dehydrogenase is used, preferably the cholesterol dehydrogenase is present in a reagent for coating a solid surface of this invention in an amount of from 1 nano-kat/l to 100 kat/l. Even more preferably, said enzyme is present in an amount of 0.1 mkat/l to 10 mkat/l. Even more preferably, said enzyme is present in an amount of 1 mkat/l to 6 mkat/l. Preferably, the cholesterol dehydrogenase is present on the test device in an amount of about 1 nano-kat/$m^2$ to about 1 kat/$m^2$, more preferably about 1 micro-kat/$m^2$ to about 10 mkat/$m^2$, even more preferably about 0.1 mkat/$m^2$ to about 1 mkat/$m^2$.

In the event that an enzyme system using any peroxidase is used, preferably the peroxidase is present in a reagent for coating a solid surface of this invention in an amount of from 1 nano-kat/l to 100 kat/l. Even more preferably, said enzyme is present in an amount of 0.1 mkat/l to 10 mkat/l. Even more preferably, said enzyme is present in an amount of 1 mkat/l to 6 mkat/l. Preferably, the peroxidase is present on the test device in an amount of about 1 nano-kat/m² to about 1 kat/m², more preferably about 1 micro-kat/m² to about 10 mkat/m², even more preferably about 0.1 mkat/m² to about 1 mkat/m².

In the amount that any other enzyme is used in a test device of this invention, preferably the enzyme is in a reagent for coating a solid surface of this invention in an amount of from 1 nano-kat/l to 100 kat/l. Even more preferably, said enzyme is present in an amount of 0.1 mkat/l to 10 mkat/l. Even more preferably, said enzyme is present in an amount of 1 mkat/l to 6 mkat/l. Preferably, the enzyme is present on the test device in an amount of about 1 nano-kat/m² to about 1 kat/m², more preferably about 1 micro-kat/m² to about 10 mkat/m², even more preferably about 0.1 mkat/m² to about 1 mkat/m².

Preferably, the system for determining the concentration of cholesterol has, in solution, a pH of about 4 to about 10, more preferably a pH of about 6 to about 8.

However, instead or in addition to a chromogen it is also possible to provide a fluorescent substance or a radioactive isotope, in order to determine the amount of cholesterol in the sample. For example, a ligand which binds to cholesterol is conjugated or otherwise labeled with a fluorescent substance or a radioactive isotope and a conjugate between the ligand and the LDL cholesterol is formed, which conjugate can for example flow into a detection lane, where the complexes of the conjugates are captured and the concentration of the conjugates are determined according to the fluorescence or radioactivity detected. Such detection systems are well known in the art and the person skilled in the art will be able to design the most appropriate system for determining the concentration of cholesterol. An example for a similar system is the BNP test by Biosite Inc. (BIOSITE DIAGNOSTICS, 11030 Roselle Street, San Diego, Calif. 92121).

Preferably, a fluorescent substance of this invention is present in a reagent for coating a solid surface of this invention in an amount of from 1 ng/100 ml to 10 g/100 ml, more preferably from about 0.1 mg/100 ml to about 1 g/100 ml, and even more preferably from about 1 mg/100 ml to about 10 mg/100 ml. Preferably, the fluorescent substance is present on the test device in an amount of about 1 microgram/m² to about 100 g/m², preferably 1 mg/m² to 10 g/m², and most preferably 100 mg/m² to 1 g/m².

Preferably, a radioactive isotope of this invention is present in a reagent for coating a solid surface of this invention in an amount of from 1 ng/100 ml to 10 g/100 ml, more preferably from about 50 ng/100 ml to about 1 g/100 ml, and even more preferably from about 100 ng/100 ml to about 1 mg/100 ml. Preferably, the radioactive isotope is present on the test device in an amount of about 1 microgram/m² to about 100 g/m², preferably 1 mg/m² to 10 g/m², and most preferably 100 mg/m² to 1 g/m².

Preferably, a chromogen of this invention is present in a reagent for coating a solid surface of this invention in an amount of from 1 ng/100 ml to 10 g/100 ml, more preferably from about 0.1 mg/100 ml to about 1 g/100 ml, and even more preferably from about 1 mg/100 ml to about 10 mg/100 ml. Preferably, the chromgen is present on the test device in an amount of about 1 microgram/m² to about 100 gm/², preferably 1 mg/m² to 10 g/m², and most preferably 100 mg/m² to 1 g/m².

Since the system for determining the concentration of cholesterol is preferably a system using a chromogen resulting in a semi-quantitative determination, it is sufficient for the Non-LDL inhibitor to inhibit the HDL/HDL-Cholesterol or activate the LDL/LDL-Cholesterol; the additional Cholesterol amount of chylomicron and VLDL does not change the result substantially. However, it is possible to add a further substance to reduce the reactivity of chylomicron-cholesterol and VLDL-cholesterol with the system for determining the concentration of cholesterol. This substance is preferably a-cyclodextrin sulphate. Thereby the result of the present test device will comprise only LDL-Cholesterol and the results will be precise. Preferred examples of this substance are:

.alpha.-Cyclodextrin,
.beta.-Cyclodextrin,
.gamma.-Cyclodextrin,
Dimethyl-.beta.-cyclodextrin,
Trimethyl-.beta.-cyclodextrin,
Hydroxyethyl-.beta.-cyclodextrin,
2-Hydroxypropyl-.alpha.-cyclodextrin,
2-Hydroxypropyl-.beta.-cyclodextrin,
Carboxymethyl-.beta.-cyclodextrin,
Glucosyl-.beta.-cyclodextrin,
Maltosyl-.alpha.-cyclodextrin,
Maltosyl-.beta.-cyclodextrin,
Partially-methyl-.beta.-cyclodextrin,
.alpha.-Cyclodextrin sulfate, and
.beta.-Cyclodextrin sulfate.

It is preferable to provide a membrane covering at least part of the reaction area to the test device of this invention, whereby the membrane is selective for interfering substances, meaning that specific molecules comprising interfering substances will be retained in the membrane and therefore not come into direct contact with the agents used in the system for determining the concentration of cholesterol, in particular the chromogen. Such specific molecules are in particular erythrocytes which would interfere with the color development. An example for such a membrane is SP100 Membrane by PALL. This membrane consists of polysulfone and is highly asymmetric. Its pore size is roughly 2 to 2.5 microns on one side, and roughly 100 times more on the other side. It is possible to provide two or more membranes, depending on the type of membrane used. For reading and interpreting the reaction result, in particular if the result is shown by a specific color, it is possible to either wipe off the molecules retained by the membranes, to detach the membrane from the test device or to read and interpret the reaction result at a part of the reaction area which is not covered by the membrane, e.g. beside the membrane or on the other "back" side—opposite the membrane—of the reaction area.

A sample according to the present invention may be any sample in which the amount of LDL-cholesterol is desired. Preferably, the sample is whole blood, plasma or serum. Also food such as butter or meat may be used as a sample in the present test device, as may other substances that are typically ingested such as dietary supplements, and other substances such as moisture cremes.

This test device allows an easy, time-efficient and cost-effective determination of the concentration of LDL-Cholesterol in a sample. A sample of the present invention need not be diluted at all, but may be diluted for instance in the event that the LDL-cholesterol level in the sample is higher than the maximum detection level of the test device. Also, a solid sample may be liquified in water or other solution to be applied to the test.

Preferably, the test device of the present invention detects and can measure about 10-500 mg LDL-cholesterol/dl sample, more preferably about 50 to 300 mg LDL-cholesterol/dl sample. When too much LDL is in a sample applied to a test device of this invention, all color dye or other visualization substances such as fluorescent compounds is used up, so for instance the color developed by the system for measuring LDL-cholesterol will not continue to develop or darken.

The amount of Non-LDL inhibitor polymer in a sample is constant despite this dilution as its properties are determined on its concentration in reference to the sample-volume, not its total amount.

FIG. 1a illustrates a side view of a test device (10) according to the present invention, comprising a solid surface (26), which is for example a paper, a membrane, or any other material conventionally used for analytical tests, optionally attached to (removably or permanently) another surface (12) to provide further support for the solid surface (26). Such an other surface (12) may be for instance flexible or inflexible, transparent or opaque, colored or clear, hard or soft. For instance, the other surface may be made of paper, plastic, cardboard. One reaction area (14) is also shown on the solid surface (26). Typically, the reaction area (14) comprises dried chemicals on at least part of the solid surface (26). The reaction area (14) of FIG. 1 includes a dried coating of Non-LDL inhibitor (16) and a dried coating of system for determining the concentration of cholesterol (18) on the same solid surface (26), and throughout the entire solid surface. An amount of sample (32) is suspended above the center of the reaction area (14), so that the sample (32) may spread throughout the reaction area (14). The sample (32) may otherwise be applied anywhere on the reaction area (14), or on a sample area (not shown) to the side of the reaction area, in which case the sample will be applied to the sample area and flow toward the reaction area and then spread throughout the reaction area. A test device of the present invention may also comprise two or more reaction areas (not shown; see for instance FIG. 6), for instance depending on the number of samples to be tested or the number of parallel tests for other substances to be carried out. Preferably, such parallel tests comprise further reaction areas for parallel testing of other health-related parameters including for instance total cholesterol, triglycerols, the presence of specific antibodies or antigens, blood type.

Non-LDL inhibitor (16) and system for determining the concentration of cholesterol (18) are for example impregnated on or in the reaction area (14) of the solid surface (26) and/or are for example covalently bound thereto. Other substances such as alpha-cyclodextrin (not shown) may also be applied to the reaction area.

Figure 1B:
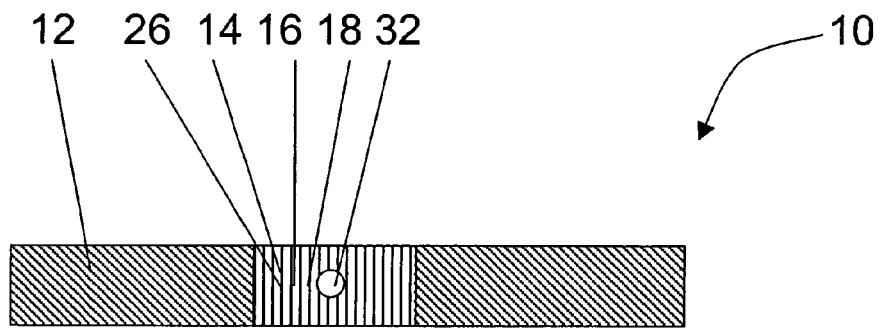
FIG. 1b is a diagram illustrating a plan view of a test device of the invention.

FIG. 1b illustrates a plan view of the test device (10) of FIG. 1a, as discussed above. In FIG. 1b, the sample (32) is newly applied to the test device, and will proceed to spread across the reaction area (14) and solid surface (26) if sufficient volume of sample (32) is present, and even to further spread across the remainder of the another surface (12).

Figure 2A:
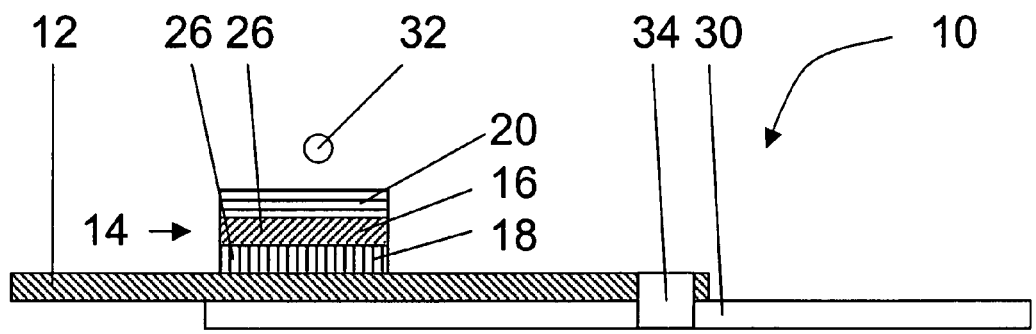
FIG. 2a is a diagram illustrating a side view of a test device of the invention.

FIG. 2a illustrates a side view of a test device (10) of this invention. Another surface (12) such as a plastic strip or cardboard or paper supports a reaction area (14) made up of two solid surfaces (26), and at least one membrane (20) covers said reaction area (14). Alternatively, the membrane (20) may cover only part of the entire reaction area, or may cover the entire reaction area and all or part of the solid surface and/or the another surface (12). The membrane (20) is selective for interfering substances, preferably for erythrocytes, to prevent erythrocytes and other substances that may interfere for instance with color development from entering the reaction area (14).

FIG. 2a also shows a reaction area (14) having a system for determining cholesterol concentration (18) on a solid surface (26) separate from and underneath a solid surface (26) having Non-LDL inhibitor (16). When the sample (32) is applied to the reaction area (14), the sample (32) will first pass through the membrane (except for interefering substances). The sample (32) may include particulate or relatively large or colored substances such as erythrocytes, as the membrane (20) will keep such from interfering with the reaction area (14). The remaining sample will then be exposed to the Non-LDL inhibitor (16) and then to system for determining cholesterol concentration (18). Each solid surface (26) can be glued or otherwise permanently or removably attached to the other solid surface (26), for instance to prevent movement (attachment not shown). The solid surface (26) having the reaction area (14) having the system for determining the concentration of cholesterol (18) may also be permanently or removably attached to the another surface (12). In FIG. 2a, the another surface (12) is attached by a rivet (34) to a wheel having a side with a colored surface (30) (colored surface not shown) where the colored surface shows colors referring to a given concentration of cholesterol as performed in the reaction area (14) of the test device (10). See FIG. 7 for an example of such colored surface. FIG. 2a shows only the edge of the wheel (30).

FIG. 2a also shows the edge and non-colored side of a wheel having a side with a colored surface (30) (color not shown) with the colors referring to a reference to a given concentration of cholesterol, as shown for instance in FIG. 7.

Figure 2B:
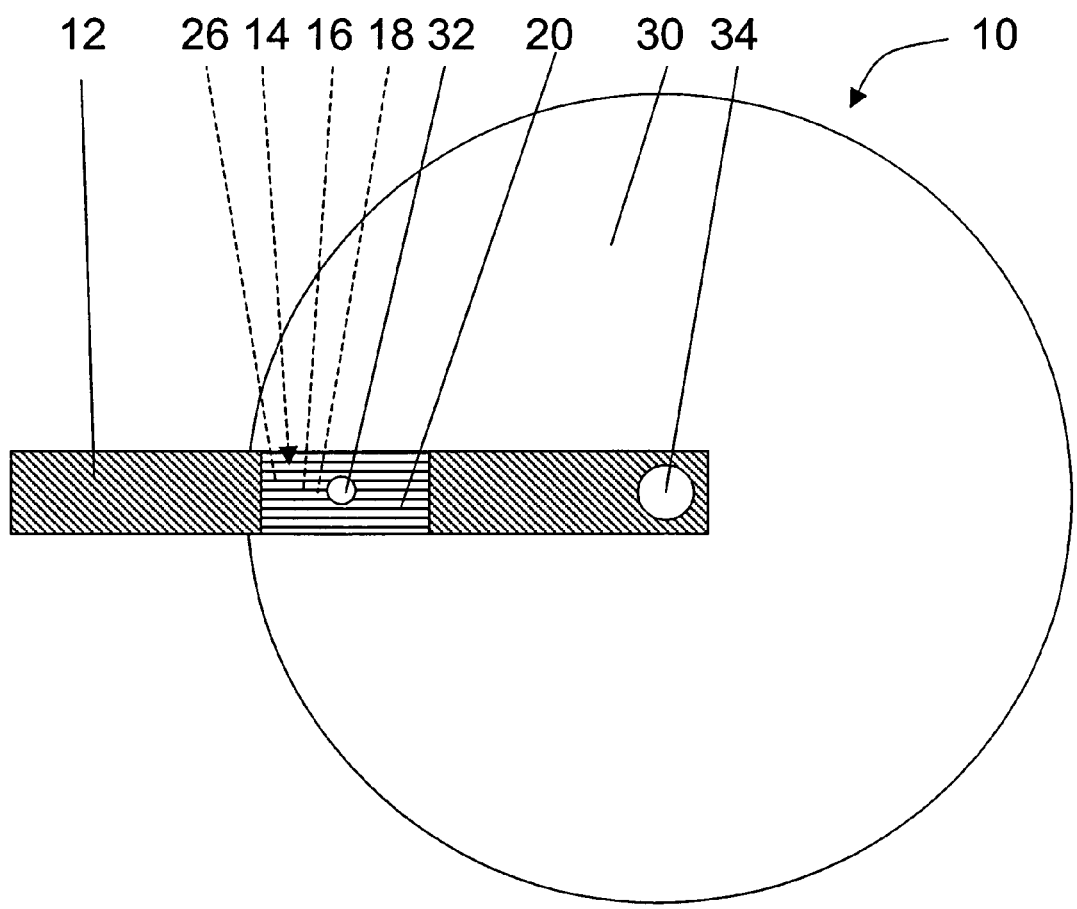
FIG. 2b is a diagram illustrating a plan view of a test device of the invention.

FIG. 2b illustrates a plan view of a test device of this invention, described as above in FIG. 2a. In FIG. 2b, the sample (32) is newly applied to the test device, and will proceed to spread across the reaction area surface and if sufficient sample volume is present to spread across the remainder of the solid surface area.

See also U.S. Pat. No. 6,558,897, for an example of a wheel-type device similar to that pictured in FIG. 2a and 2b and in FIGS. 5-7.

EXAMPLE 1

In order to demonstrate that the test device of the present invention determines the concentration of LDL-Cholesterol, LDL-Cholesterol determination was carried out in liquid with the following solutions:

Solution 1: LDL-Cholesterol=76.5 mg/dl (±15 mg/dl), HDL-cholesterol=17.5 mg/dl (±3.5 mg/dl), total cholesterol=132 mg/dl (±17.5 mg/dl ). (Solution 1 is Lipid Control 1 from Pointe Scientific Inc., diluted 1:1 with water.) (Pointe Scientific, Inc., 1025 John A. Papalas Drive, Lincoln Park, Mich. 48146 U.S.A.)

Solution 2: LDL-Cholesterol=31 mg/dl (±8 mg/dl),HDL-cholesterol=80 mg/dl (±19 mg/dl), total cholesterol=145 mg/dl (±23 mg/dl) (Lipid Control 2 from Pointe Scientific Inc., undiluted).

The difference between the amount of total cholesterol and of LDL and HDL cholesterol in each of these solutions includes for instance IDL, VLDL.

Two small (about 0.5 cm by 0.5 cm) pieces of SP100 membrane were prepared. The pieces were cut to be the same size. One piece of membrane was dipped into Solution 1, and the other piece of membrane was dipped into Solution 2, until identical volumes of Solutions 1 and 2 were soaked into each membrane.

The membranes were then immersed in 2 ml of a reagent prefilled into two centrifuge tubes of the same size (one membrane per centrifuge tube). The reagent is suitable for a reaction area of a test device of this invention, having non-LDL inhibitor and a system for determining the concentration of cholesterol. (200 microliters of a solution having cholesterol esterase 2.9 mkat/l, cholesterol oxidase 2.4 mkat/l, horseradish peroxidase 2.6 mkat/l, tetramethylbenzidine chromogen (TMB) 1 g/100 ml, trisbuffer 0.1 M pH=6.7 and 25% polymer POE-POP with an average molecular mass ranging from 1100 to 6500, diluted 1:10 with distilled water).

The membranes were immersed in the reagent for 2 minutes. Then the immersed membranes were subjected to centrifugation (13,000 rpm, 3 min, room temperature), in an Eppendorf MiniSpin centrifuge (Eppendorf AG, Barkhausenweg 1, 22339 Hamburg Germany). Solution in the centrifuge tubes was decanted into separate vessels and diluted with equivalent amounts of water. (Source of enzymes: Sorachim, Paris, France. Sourse of Tris, TMB: SIGMA-ALDRICH, Vienna, Austria. Source of POE-POP: Depha, Wien, Austria). Note that while horseradish peroxidase is specified here, other peroxidases are useful in the context of this invention.

Figure 3:
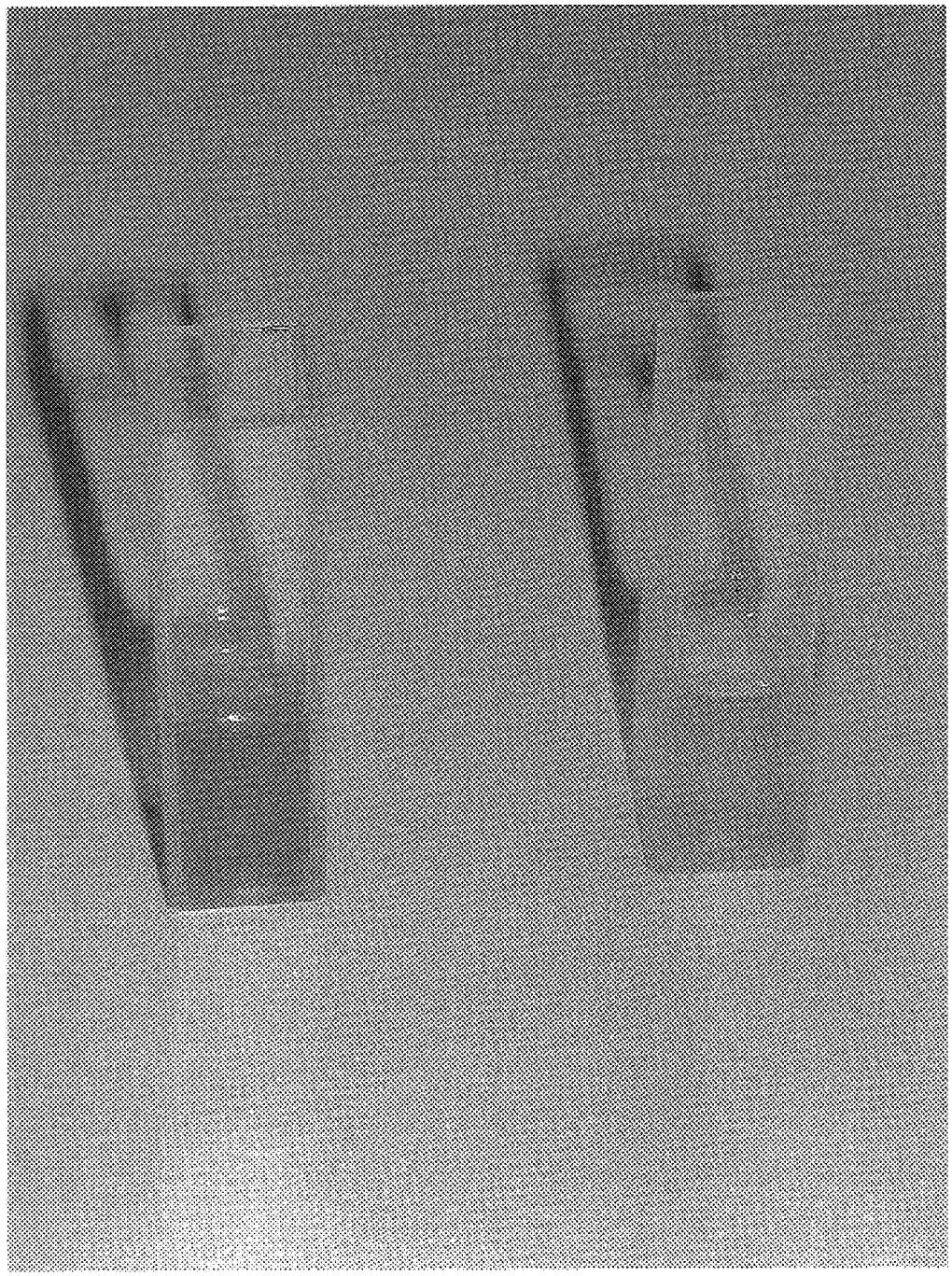
FIG. 3 is a color photograph showing the result of a test in liquid showing that the present invention determines the amount of LDL-cholesterol in a sample.

FIG. 3 shows the results of this experiment. The vessel on the left shows the results achieved with Solution 1 and the vessel on the right shows the results achieved with an identical volume of Solution 2. Solution 1, having an about 2.5 fold higher LDL-Cholesterol level than Solution 2, gives a much stronger visual color signal than Solution 2. The same protocol as discussed above, without the addition of polymer POE-POP to the reagent in the centrifuge tube, tests for total cholesterol instead of just LDL-cholesterol. Following such protocol without POE-POP shows a slightly deeper color with Solution 2 than Solution 1(not shown), in keeping with the slightly higher amount of total cholesterol in Solution 2 than Solution 1.

This test shows that the polymer POE-POP inhibits the reaction of the system for detecting the concentration of cholesterol with HDL-cholesterol and other non-LDL cholesterol, so that the enzymes of the system for detecting the concentration of cholesterol detect only LDL-Cholesterol. Without the presence of the polymer POE-POP, non-LDL-cholesterol is not kept from reacting with the system for detecting the concentration of cholesterol, and total cholesterol is determined by the system for detecting the concentration of cholesterol. In such a case, the color in the two vessels is similar (not shown). Without being bound by theory, this inhibition of non-LDL-cholesterol by non-LDL inhibitor such as POE-POP may be caused by the coating of non-LDL substances with polymer.

EXAMPLE 2

Figure 4:
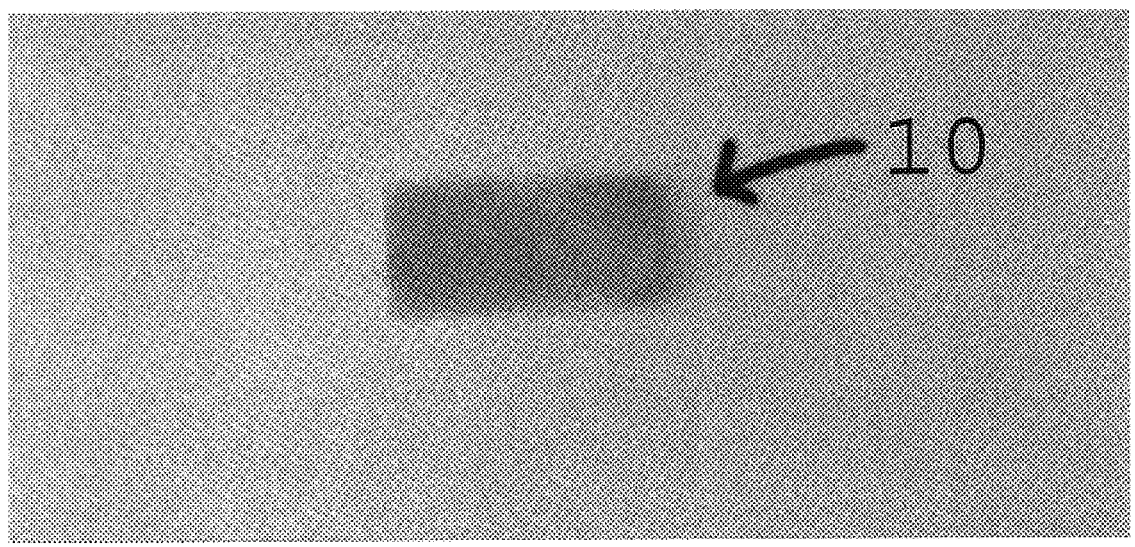
FIG. 4 is a color photograph showing a plan view of a working test device of the invention.

FIG. 4 shows a color photograph of a test device (10) of this invention. Serum from fresh whole human blood was applied to the test device (10). The test device (10) has one solid surface comprising one reaction area having non-LDL inhibitor and system for determining the concentration of cholesterol. The test device (10) is similar to the illustration provided in FIG. 1, however, the another surface (Reference number 12 of FIG. 1) is not present. The reaction area (Reference number 14 of FIG. 1) covers the entire solid surface (Reference number 26 of FIG. 1). The solid surface is Office 480 type paper, 80 g/m2 (Viking Direkt GesmbH, Pregarten, Austria).

The reaction area comprises a dried coating of the undiluted reagent described in Example 1 above, having cholesterol esterase 2.9 mkat/l, cholesterol oxidase 2.4 mkat/l, peroxidase 2.6 mkat/l, tetramethylbenzidine chromogen (TMB) 1 g/100 ml, trisbuffer 0.1 M pH=6.7 and 25% polymer POE-POP with an average molecular mass ranging from 1100 to 6500. The solid surface of the Example shown in FIG. 4 has the following visible dimensions: 0.8 cm by 0.3 cm (depth not visible). Independent determination of LDL-cholesterol was determined by Hitachi analyzer to be 153 mg/dl. As the sample was serum, no membrane was necessary for this reacton to take place.

EXAMPLE 3

Figure 5:
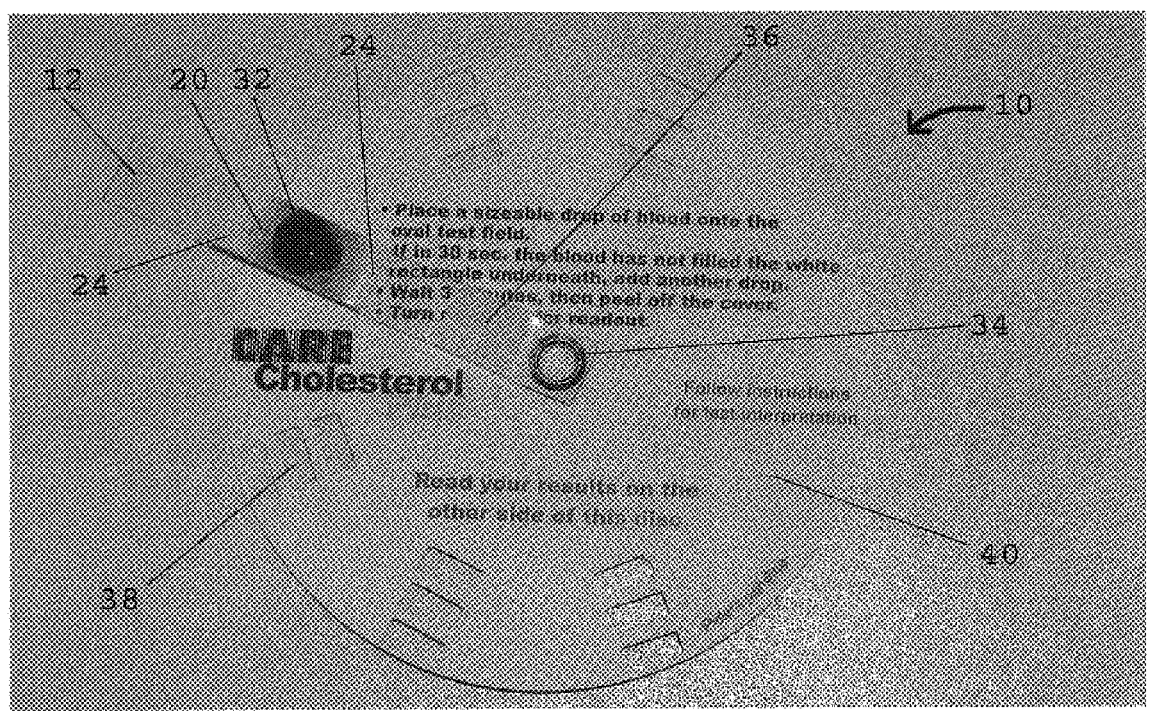
FIG. 5 is a color photograph showing a plan view of a working test device of the invention, immediately after application of a whole blood sample to the test device.
Figure 6:
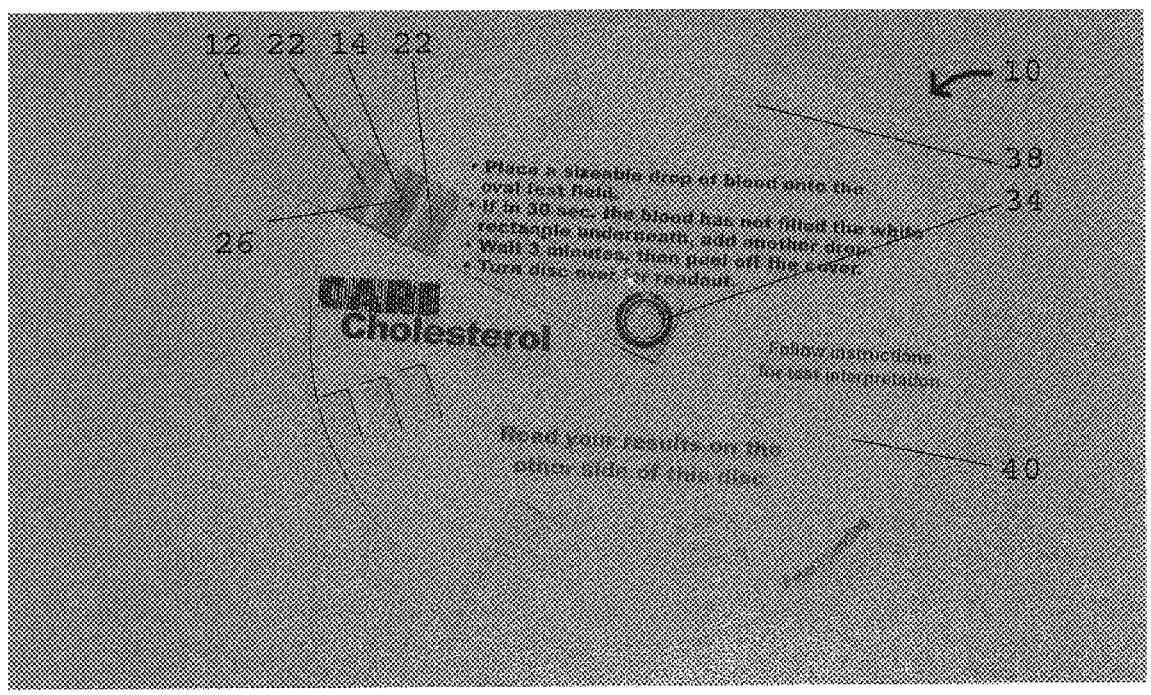
FIG. 6 is a color photograph showing a plan view of a working test device of FIG. 5, three minutes after applying the blood sample.

FIGS. 5-7 are color photographs showing a preferred test device (10) of this invention, ready for commercial use, in three stages: immediately after application of a whole blood sample (FIG. 5), three minutes after application of the sample (FIG. 6), and 3 more minutes after taking the photograph shown in FIG. 6 (FIG. 7).

In FIG. 5, a test subject pricked own skin and applied one large drop of fresh whole blood as a sample (32) to the blood separation membrane (20) of this test device (10). The solid surface and reaction area for LDL-cholesterol of the test device (10) of FIG. 5 (shown in FIGS. 6 and 7) were made in a manner similar to the test device of Example 2 and FIG. 4, by soaking the reaction area of a solid surface in the undiluted reagent of Example 2 (cholesterol esterase 2.9 mkat/l, cholesterol oxidase 2.4 mkat/l, peroxidase 2.6 mkat/l, tetramethylbenzidine chromogen (TMB) 1 g/100 ml, tris buffer 0.1 M pH=6.7 and 25% polymer POE-POP with an average molecular mass ranging from 1100 to 6500) to prepare an LDL-cholesterol reaction area on paper, and allowing the reaction area to air dry. Further, the solid surface is attached to another surface (12) by applying glue from a glue stick (UHU stick, UHU Austria Ges.m.b.H. A-1020 Wien, Austria). In alternative embodiments the solid surface may be attached using other adhesive, glue, rivet, bracket, solid cover or physically such as applying pressure or temperature. As shown in FIG. 5, another surface (12) in the form of a plastic arm is attached by a rivet (34) (so the arm may be turned around the rivet) to a wheel (30) having a colored surface with colored reference areas. See also for example the device described in U.S. Pat. No. 6,558,897.

Three strips of white paper (not shown) (0.3 cm by 0.8 cm, Office 480 type paper, 80 g/m2 (Viking Direkt GesmbH, Pregarten, Austria)) were prepared for attachment to the another surface in the form of a plastic arm (12) (6 cm by 0.8 cm), and attached to the transparent plastic arm with UHU stick. Each strip was coated with a different reagent, to test for the occurrence and amount of a different substance in the sample. The middle strip (as seen in FIGS. 6 and 7) was coated with a reagent according to the undiluted reagent discussed above and in FIG. 4, to prepare a reaction area to test for LDL-cholesterol. The strip farthest from the rivet (34) was coated with an undiluted reagent similar to that described in FIG. 4, but not having any POE-POP or any other non-LDL inhibitor, to test for total cholesterol of the sample. The strip nearest the rivet (34) was coated with an undiluted reagent similar to that described in FIG. 4, except that instead of cholesterol esterase and cholesterol oxidase, the reagent had lipase (5 mkat/l), glycerin kinase (3.3 mkat/l), L-glycerol-3-phosphate oxidase (3.4 mkat/l) and ATP (20 mg/ml), to test for the triglyceride content of the sample. The blood separation membrane (20) was placed on top of all three strips and directly contacts the reaction area (not shown)to faciliate transmission of sample (except for any interfering substances retained by the membrane) to reaction area. The top left portion of the membrane (20) as pictured here rests on a strip of adhesive paper (24) (Zweckform GmbH, Oberlaindem, Germany), as does a bottom right portion of the membrane (20), to help hold the membrane (20) in place and ensure the membrane (20) comes off properly when removed. Also, the strip of adhesive paper prevents blood flowing around the membrane which may happen without the paper. Also present, but not easily visible in FIG. 5 (no reference number provided), is a transparent label covering the entire plastic arm, where the transparent label has an elliptical hole to avoid covering the sample (KMC Vienna, Austria) (5 cm by 0.8 cm).

In the test device of FIG. 5, the spacing between the three strips of paper attached to the plastic arm (shown in FIGS. 6 and 7) is 0.15 cm. The wheel (30) has a diameter of 7.6 cm and a thickness of 0.025 cm. The windows (38) of the wheel are 0.30 cm by 0.7 cm. The blood separation membrane (PALL, SP-100) is 1.5 cm by 0.8 cm. A paper portion to faciliate tearing off the adhesive (36) is provided near the rivet (34). The wheel having a colored surface (30) further has a back surface (40) with directions for use of the test device.

The color photograph shown in FIG. 5 was taken immediately after application of the sample to the test device. Diffusion of the blood across the membrane may be seen on either side of the blood sample (32). The membrane (20) kept erythrocytes from the sample (32) from coming into contact with the reaction area of the solid surface of the test strip, and was removed from the reaction area 3 minutes after application of the blood to the membrane after application of the subject's blood as a sample (32). The blood (32) (minus erythrocytes) came into contact with the reaction area (14) of the test device (10).

FIG. 6 shows the reaction device after removal of the blood separation membrane. The red smear of the blood diffusing from the blood sample (32), visible in FIG. 5, is no longer apparent, as the membrane (20) kept the red blood cell component of the sample (32) away from the reaction area.

The device of FIG. 5 states among other things that the present invention is "Patent pending". FIGS. 5-7 embody a commercial embodiment of this invention prepared for sale after filing of this application. The embodiment of FIGS. 5-7 is a preferred embodiment of this invention.

FIG. 6 shows the test device (10) of FIG. 5 three minutes after applying the sample (32) to the test device (10) and removing the blood separation membrane (20). Three strips of different colors are apparent on the test device (10), corresponding to the three strips of paper discussed in FIG. 5, above. Qualitatively, the center strip of the three strips is a reaction area (14) of the present invention, that shows the presence of LDL-cholesterol in the sample. The strip farthest (22) from the rivet (34) of the test device (10) shows the presence of total cholesterol; the strip closest (22) to the rivet (34) shows the presence of triglycerides. Without being bound by theory, it is believed that the POE-POP affects the color formation by the system for determining the cholesterol concentration on the solid surface (14), because the color formed in the LDL reaction area (14) (green) is of a different range of colors than the color formed by the nearly identical test for total cholesterol (without POE-POP; turquoise).

FIG. 7 shows the test device (10) of FIGS. 5 and 6, turned over three minutes after the photograph shown in FIG. 6, so the solid surface (26) having the reaction area for LDL-cholesterol (14) and the other strips (22) is underneath the wheel (30) having windows (38) within a colored surface with reference areas. The reference areas allow for a quantitative analysis of each colored band. In this case, the amount of total cholesterol (strip (22) farthest from rivet (34)), LDL-cholesterol (center strip (14)), and triglycerides (strip (22) nearest rivet (34)) is compared with the reference colors on the wheel (30), shown in a yellow triangle and through windows (38) on the test device (10). The reference colors in the yellow triangle indicate that a matching color on the test device would mean a healthy and desirable result for the subject.

Figure 8:
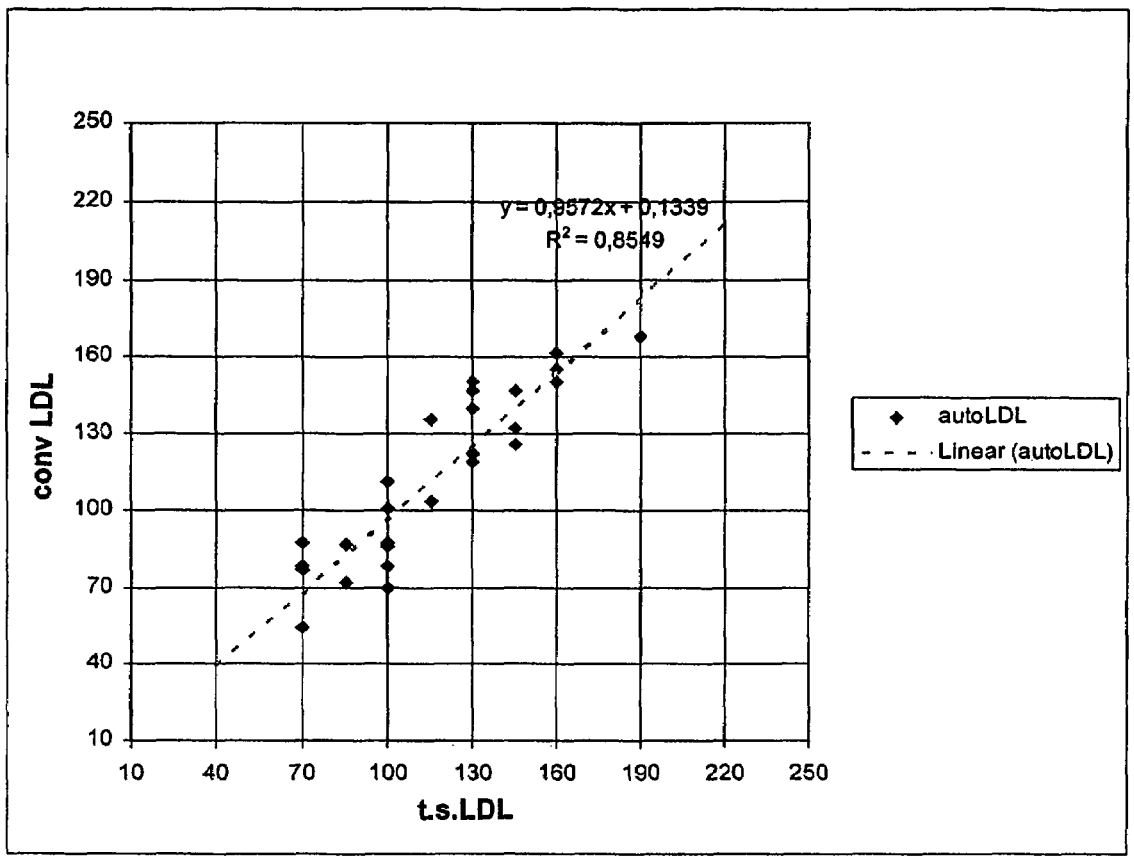
FIG. 8 is a graph comparing results obtained by patients reading a result from a test device of this invention and results measured by a conventional LDL-Cholesterol test.

FIG. 8 is a graph comparing the results obtained from determining the concentration of cholesterol with the inventive test device described herein and from a conventional LDL-Cholesterol test. Overall, the curve shows that a good correlation and specificity is achieved with LDL-cholesterol measurements made by the present invention, compared with conventional methods of measuring LDL-cholesterol.

To using a test device of this invention to determine the LDL-cholesterol concentration of a sample, blood was taken from 26 different patients and applied to a test device as described in FIGS. 5-7. Each patient analyzed his or her own test device by comparing the color of his or her own LDL-cholesterol result on the device with the colored reference areas on the wheel of the test device and determining the amount of LDL-cholesterol found therein. In FIG. 8, "t.s.LDL" refers to results determined by a patient from his or her own test device. (Note that some numbers on the graph are the same as the reference numbers on the wheel shown in FIG. 7, and some numbers are half-way between such numbers.)

The t.s.LDL readings of LDL-cholesterol were compared with LDL-concentrations of the same blood sample measured according to the Pointe Scientific Inc. LDL-cholesterol test method on a conventional Hitachi analyzer: A blood sample was taken from each subject, left to sit 2 hours, and subjected to centrifugation to remove cellular components of the blood. (13,000 rpm, 3 min, room temp, in Eppendorf MiniSpin centrifuge (Eppendorf AG, Barkhausenweg 1, 22339 Hamburg Germany)). The results of the conventionally measured LDL-cholesterol analysis of the samples is represented as "conv LDL" or "autoLDL" in FIG. 8.

A comparison of the t.s.LDL and convLDL readings as shown in FIG. 8 shows an $R^2$ of 0.85 (1.00 being a perfect correlation of t.s.LDL with convLDL). This is a very good correlation, in particular for a non-instrument test performed by human subjects rather than by an analytical machine.

The invention claimed is:

1. Test device for LDL-cholesterol comprising a continuous solid surface with a reaction area on the continuous solid surface, said reaction area comprising, in dry form,
a Non-LDL inhibitor and
a system for determining the concentration of cholesterol,
   wherein said Non-LDL inhibitor and said system for determining the concentration of cholesterol are at least one of the group consisting of impregnated on, impregnated in and covalently bound to the same continuous solid surface.

2. The test device according to claim 1 wherein said Non-LDL inhibitor is a polymer.

3. The test device according to claim 1 wherein said Non-LDL inhibitor is a nonionic polymer.

4. The test device according to claim 1 wherein said Non-LDL inhibitor is at least one selected from the group consisting of polyoxymethylene, polyoxyethylene, polyoxypropylene, polyoxybutylene, dodecylbenzene, higher alcohol, and fatty acid.

5. The test device according to claim 4, wherein said non-LDL inhibitor is at least one selected from the group consisting of polyoxymethylene, polyoxyethylene, polyoxypropylene, and polyoxybutylene.

6. The test device according to claim 1 wherein said Non-LDL inhibitor is a copolyether comprising polyoxyethylene and polyoxypropylene.

7. The test device according to claim 6 wherein said copolyether has an average molecular mass X, said X being selected from the group consisting of about 500 to about 10000 Da and about 1000 to about 6500 Da.

8. The test device according to claim 7, wherein X is about 1000 to about 6500 Da.

9. The test device according to claim 1 wherein said Non-LDL inhibitor is provided on the reaction area in a concentration selected from the group consisting of about 0.01 to about 500 g/m² and about 3 to about 30 g/m².

10. The test device according to claim 9, wherein said concentration of Non-LDL inhibitor is about 3 to about 30 g/m².

11. The test device according to claim 1 wherein said Non-LDL inhibitor is an anti-HDL antibody.

12. The test device according to claim 1 wherein said system for determining the concentration of cholesterol comprises an enzyme system comprising cholesterol esterase and cholesterol oxidase.

13. The test device according to claim 1 wherein said system for determining the concentration of cholesterol comprises an enzyme system comprising cholesterol esterase and cholesterol dehydrogenase.

14. The test device according to claim 1 wherein said system for determining the concentration of cholesterol comprises a chromogen.

15. The test device according to claim 14 wherein said test device comprises at least one reference area comprising a colored surface as reference to a given concentration of cholesterol.

16. The test device according to claim 14 wherein said test device comprises at least two reference areas each comprising a colored surface as references to given concentrations of cholesterol and said reaction area is at least partly movably attached to said at least two reference areas in order to compare color developed by said chromogen on said reaction area with said colored surfaces of said at least two reference areas.

17. The test device according to claim 16, wherein said reaction area comprises cholesterol esterase; one enzyme type selected from the group consisting of cholesterol dehydrogenase and cholesterol oxidase; polymer POE-POP; tetramethyl benzidine and peroxidase.

18. The test device according to claim 17, wherein said cholesterol esterase is present in an amount of about 0.1 mkat/m² to about 1 mkat/m²; said cholesterol dehydrogenase, if present, is present in an amount of about 0.1 mkat/m² to about 1 mkat/m²; said cholesterol oxidase, if present, is present in an amount of about 0.1 mkat/m₂ to about 1 mkat/m₂; said polymer POE-POP has an average molecular mass of 1100 to 6500 and is present in an amount of about 3 to about 30 g/m²; said tetramethyl benzidine is present in an amount of about 1 mg/m² to about 10 g/m²; and said peroxidase is present in an amount of about 0.1 mkat/m² to about 1 mkat/m².

19. The test device according to claim 1 wherein said system for determining the concentration of cholesterol comprises a fluorescent substance.

20. The test device according to claim 1 wherein said system for determining the concentration of cholesterol comprises a radioactive isotope.

21. The test device according to claim 1 wherein said reaction area is further provided with a substance that reduces reactivity of chylomicron-cholesterol and VLDL-cholesterol with the system for determining the concentration of cholesterol.

22. The test device according to claim 21 wherein said substance is α-cyclodextrin sulfate.

23. The test device according to claim 1 further comprising at least one membrane covering at least part of said reaction area, said membrane being selective for interfering substances.

24. The test device according to claim 23 wherein said membrane is selective for erythrocytes.

25. Method for determining a concentration of LDL-Cholesterol in a sample comprising the steps of:
 (a) providing a test device according to claim 1,
 (b) applying to said reaction area of said device said sample,
 (c) letting said sample react with said non-LDL inhibitor and said system in order to obtain a reaction result, and
 (d) determining the concentration of cholesterol in the sample with said reaction result.

26. The method according to claim 25 wherein said Non-LDL inhibitor is a polymer.

27. The method according to claim 25 wherein said Non-LDL inhibitor is a nonionic polymer.

28. The method according to claim 25 wherein said Non-LDL inhibitor is at least one selected from the group consisting of polyoxymethylene, polyoxyethylene, polyoxypropylene, polyoxybutylene, dodecylbenzene, higher alcohol, and fatty acid.

29. The method according to claim 25 wherein said Non-LDL inhibitor is a copolyether comprising polyoxyethylene and polyoxypropylene.

30. The method according to claim 29 wherein said copolyether has an average molecular mass X, said X being selected from the group consisting of about 500 to about 10000 Da and about 1000 to about 6500 Da.

31. The method according to claim 30, wherein X is about 1000 to about 6500 Da.

32. The method according to claim 25 wherein said Non-LDL inhibitor is provided on said reaction area in a concentration selected from the group consisting of about 0.01 to about 500 g/m² and about 3 to about 30 g/m².

33. The method according to claim 32, wherein the concentration of Non-LDL inhibitor is about 3 to about 30 g/m².

34. The method according to claim 25 wherein said Non-LDL inhibitor is an anti-HDL antibody.

35. The method according to claim 25 wherein said system for determining the concentration of cholesterol comprises an enzyme system comprising cholesterol esterase and cholesterol oxidase.

36. The method according to claim 25 wherein said system for determining the concentration of cholesterol comprises an enzyme system comprising cholesterol esterase and cholesterol dehydrogenase.

37. The method according to claim 25 wherein said system for determining the concentration of cholesterol comprises a chromogen.

38. The method according to claim 37 wherein said test device comprises at least one reference area comprising a colored surface as reference to a given concentration of cholesterol.

39. The method according to claim 37 wherein said test device comprises at least two reference areas each comprising a colored surface as references to given concentrations of cholesterol and said reaction area is at least partly movably attached to said at least two reference areas in order to compare color developed by said chromogen on said reaction area with said colored surfaces of said at least two reference areas.

40. The method according to claim 37 further comprising at least one membrane covering at least part of said reaction area, said membrane being selective for interfering substances.

41. The method according to claim 40 wherein said membrane is selective for erythrocytes.

42. The method according to claim 37 wherein said sample is selected from the group consisting of whole blood, serum, a food, a dietary supplement and moisture cream.

43. The method according to claim 25 wherein said system for determining the concentration of cholesterol comprises a fluorescent substance.

44. The method according to claim 25 wherein said system for determining the concentration of cholesterol comprises a radioactive isotope.

45. The method according to claim 25 wherein said reaction area is further provided with a substance that reduces reactivity of chylomicron-cholesterol and VLDL-cholesterol with the system for determining the concentration of cholesterol.

46. The method according to claim 45 wherein said reaction area further comprises α-cyclodextrin sulfate.

47. The test device according to claim 1, wherein said Non-LDL inhibitor and system for determining the concentration of cholesterol are in a same physical space of the reaction area.

48. The test device according to claim 1, wherein the non-LDL inhibitor is polyoxyethylene-polyoxypropylene having an average molecular mass of from 1100 to 6500 Da.

\* \* \* \* \*